United States Patent [19]

Ballantyne

[11] Patent Number: 5,582,583

[45] Date of Patent: Dec. 10, 1996

[54] DYNAMIC POSTURAL STABILITY SPLINT

[75] Inventor: Jennifer Ballantyne, Perth, Australia

[73] Assignee: Second Skin Pty Ltd., Perth, Australia

[21] Appl. No.: 256,119

[22] PCT Filed: Dec. 24, 1992

[86] PCT No.: PCT/AU92/00684

§ 371 Date: Jun. 23, 1994

§ 102(e) Date: Jun. 23, 1994

[87] PCT Pub. No.: WO93/12739

PCT Pub. Date: Jul. 19, 1993

[30] Foreign Application Priority Data

Dec. 24, 1991 [AU] Australia ................... PL 0162

[51] Int. Cl.⁶ ....................................................... A61F 5/00
[52] U.S. Cl. ................... 602/5; 602/19; 602/20; 602/23; 2/69; 2/243.1
[58] Field of Search ................... 602/19, 20, 23, 602/26, 5; 2/409, 69, 109, 243.1, 255; 450/74–76, 143

[56] References Cited

U.S. PATENT DOCUMENTS

| | | | |
|---|---|---|---|
| 2,632,178 | 3/1953 | Kennedy | 602/19 X |
| 2,687,129 | 8/1954 | Talkish . | |
| 2,719,301 | 10/1955 | Witkower | 2/255 X |
| 2,888,931 | 6/1959 | Schaumer | 450/74 X |
| 2,900,984 | 8/1959 | Cunningham | 450/143 X |
| 3,045,678 | 7/1962 | Geimer . | |
| 3,116,735 | 1/1964 | Geimer . | |
| 3,173,421 | 3/1965 | Steiner | 450/74 X |
| 3,606,891 | 2/1971 | Marcario et al. | 450/76 X |
| 4,400,832 | 8/1983 | Kinder | 2/409 X |
| 4,698,847 | 10/1987 | Yoshihara | 2/69 |
| 5,109,546 | 5/1992 | Dicker | 2/69 X |
| 5,154,690 | 10/1992 | Shiono | 602/26 X |
| 5,210,877 | 5/1993 | Newnan | 2/243.1 X |
| 5,263,923 | 11/1993 | Fujimoto | 602/62 |

FOREIGN PATENT DOCUMENTS

| | | |
|---|---|---|
| 20173/76 | 12/1976 | Australia . |
| 18164/83 | 8/1983 | Australia . |
| 15544/33 | 12/1993 | Australia . |
| 0410904A1 | 7/1990 | European Pat. Off. . |
| 791351 | 6/1935 | France . |
| 2659547A1 | 3/1990 | France . |
| WO91/01704 | 2/1991 | WIPO . |
| WO92/07527 | 5/1992 | WIPO . |

OTHER PUBLICATIONS

PCT International Search Report PCT/AU 92/00684, 24 Dec. 1992.
1–288255 (A); dated 20 Nov. 1989; Auxiliary Mounting Glove.

*Primary Examiner*—Linda C. Dvorak
*Attorney, Agent, or Firm*—Merchant, Gould, Smith, Edell, Welter & Schmidt, P.A.

[57] ABSTRACT

A dynamic postural stability splint in the form of a garment (10), the garment comprising a plurality of pieces of flexible elastic material connected together to form the garment (10). Selected pieces (12) of the flexible elastic material are configured and positioned in the garment (10) so as to provide lines of pull (14) on the wearer's body in predetermined directions whereby, in use, the garment (10) can help to improve postural stability of the wearer. The dynamic splint is particularly advantageous in its application to children and adolescents with cerebral palsy. The garment may take the form of a body suit (10), or be designed for individual limbs of the wearer in the form of a hand splint, arm splint, leg splint, etc. A method of manufacturing a dynamic splint and a method of treating postural instability are also described.

8 Claims, 14 Drawing Sheets

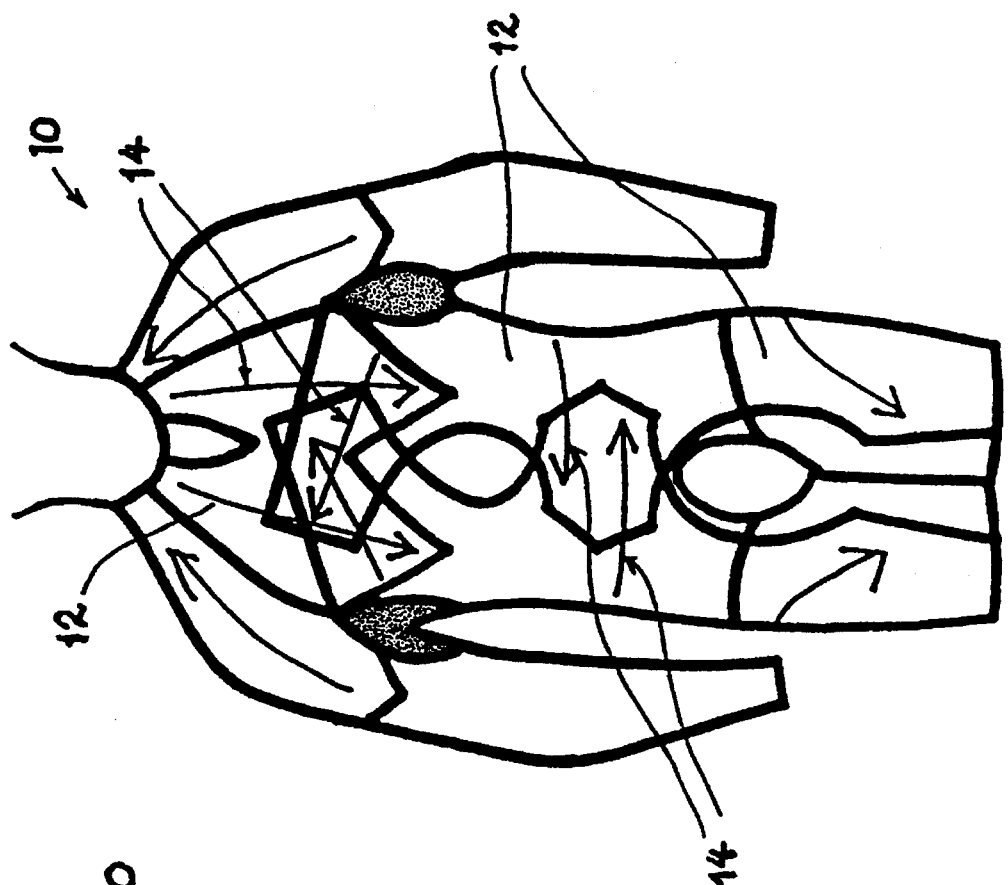
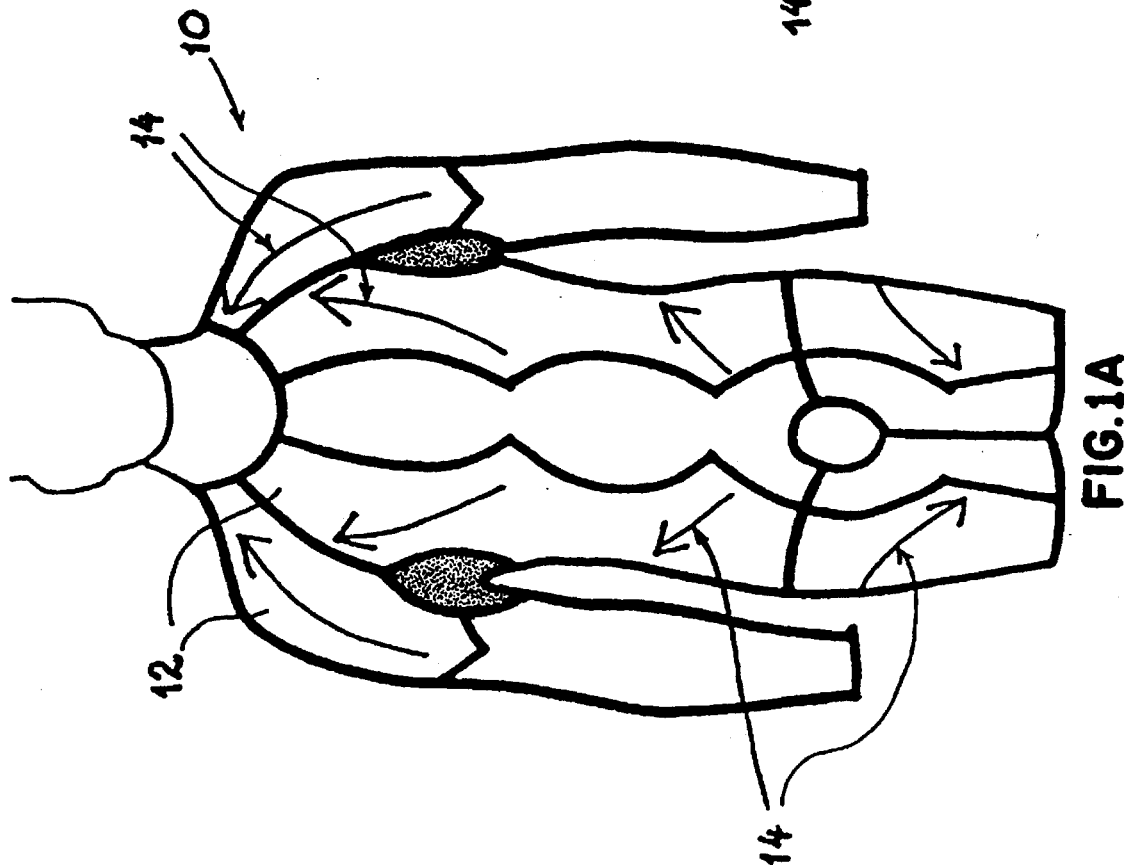
FIG. 1B
FIG. 1A

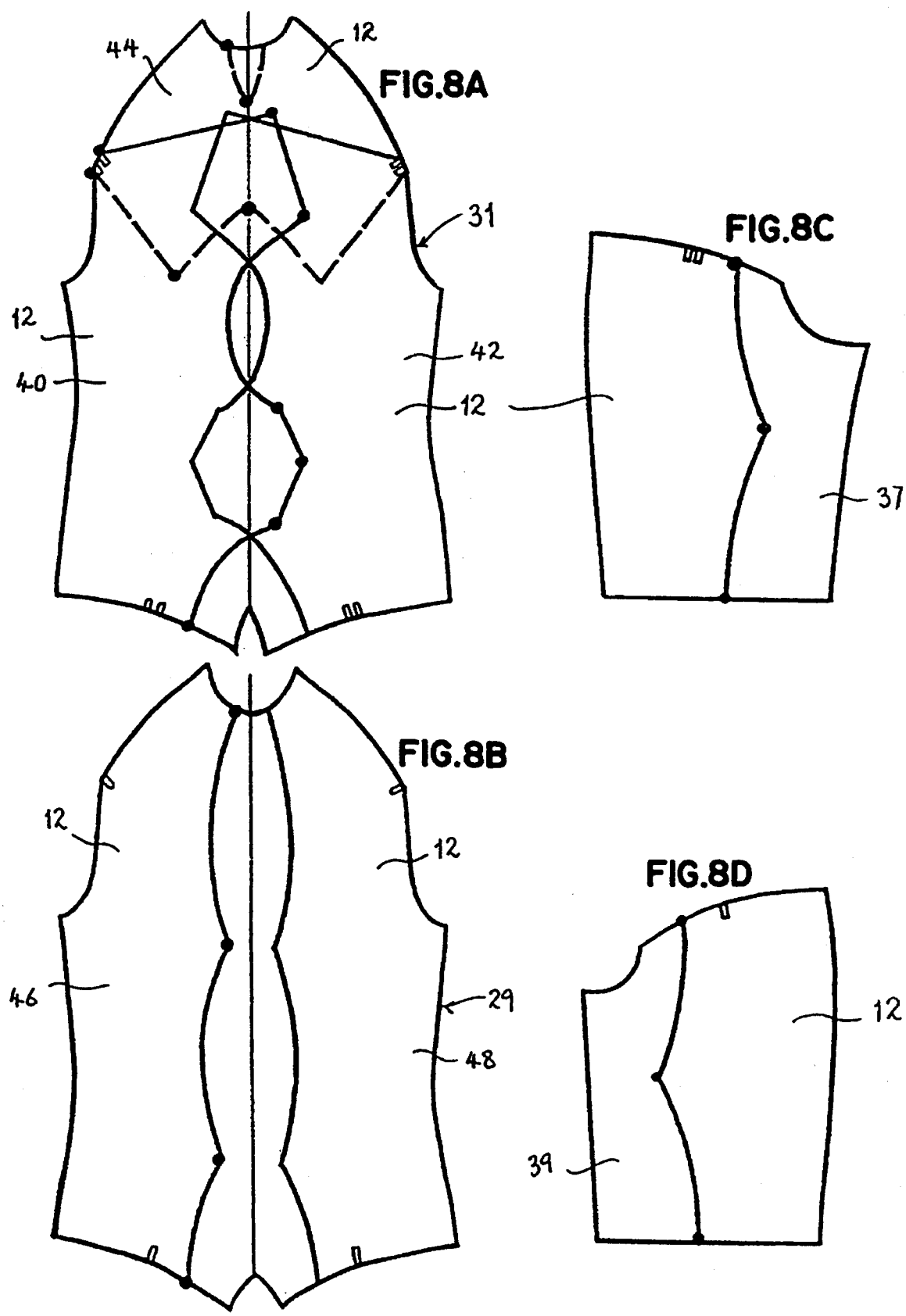

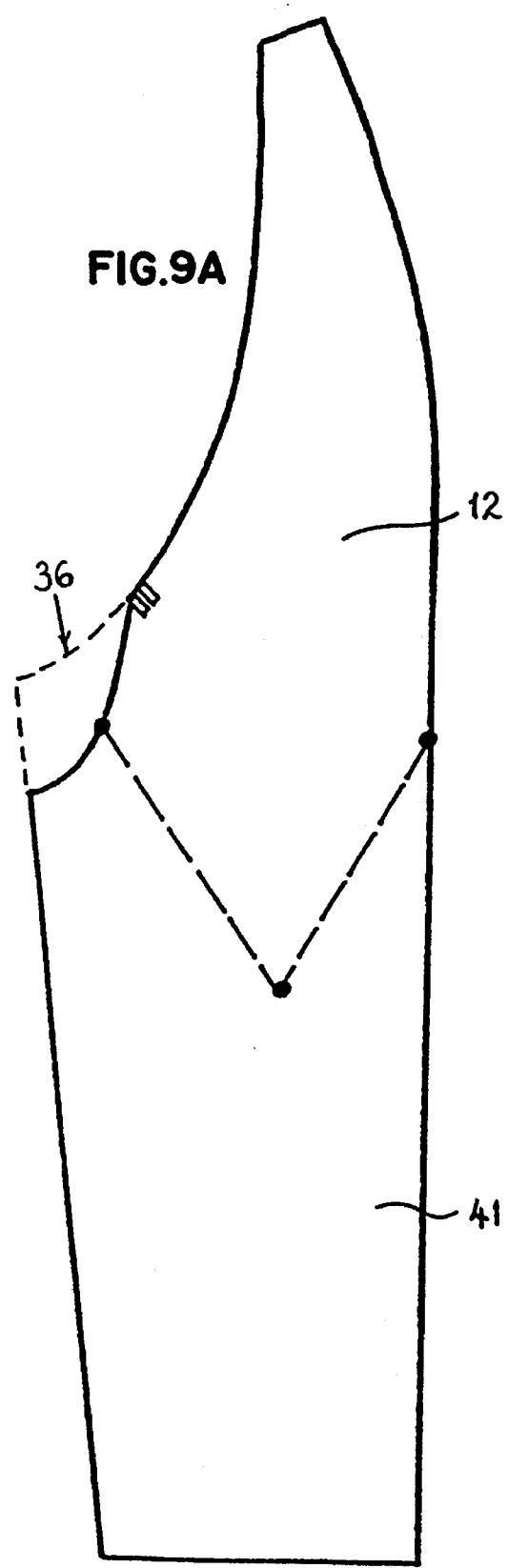
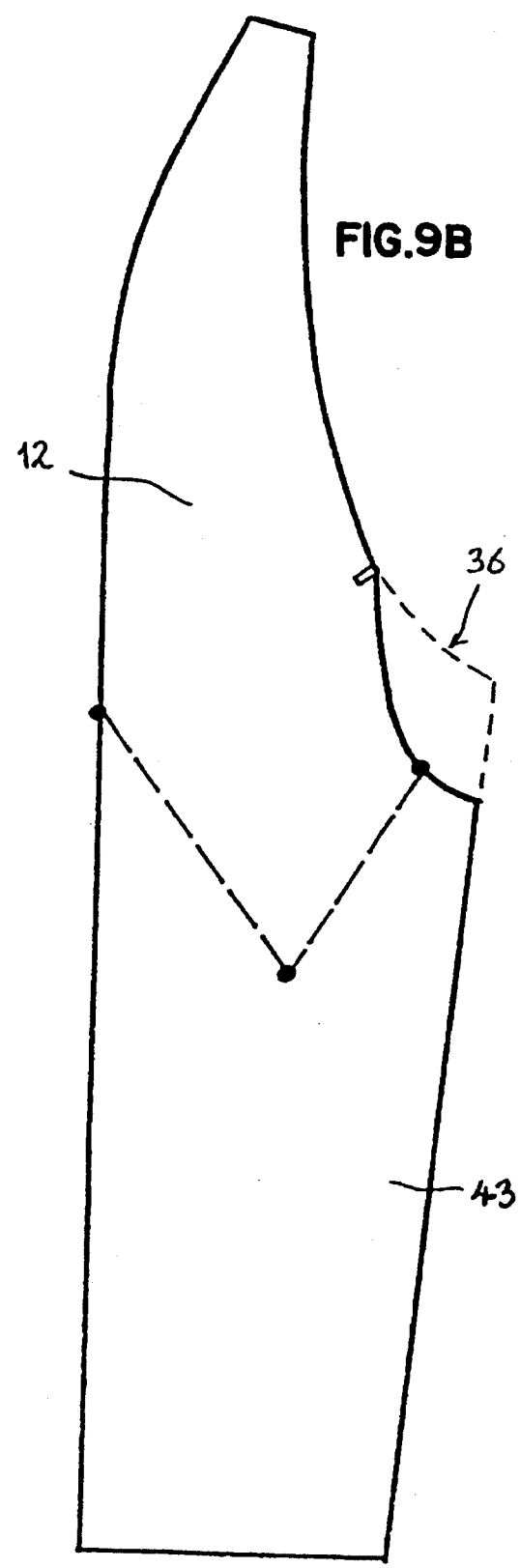

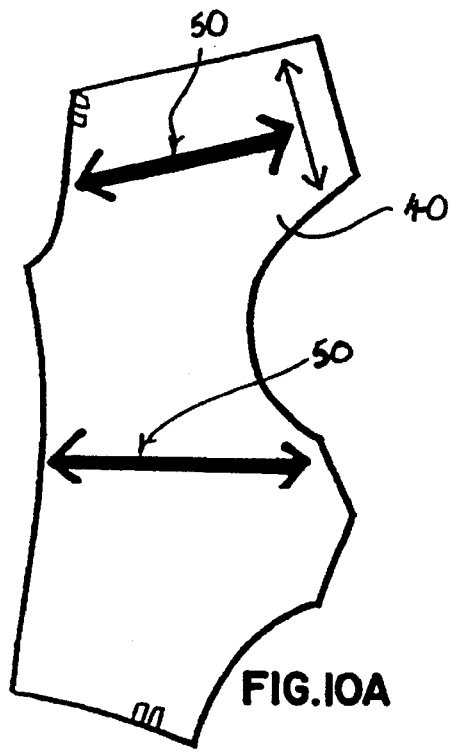
FIG.10A
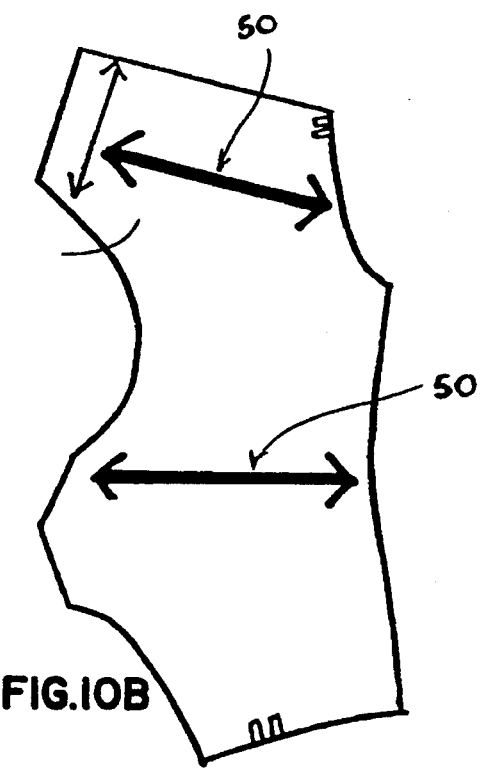
FIG.10B
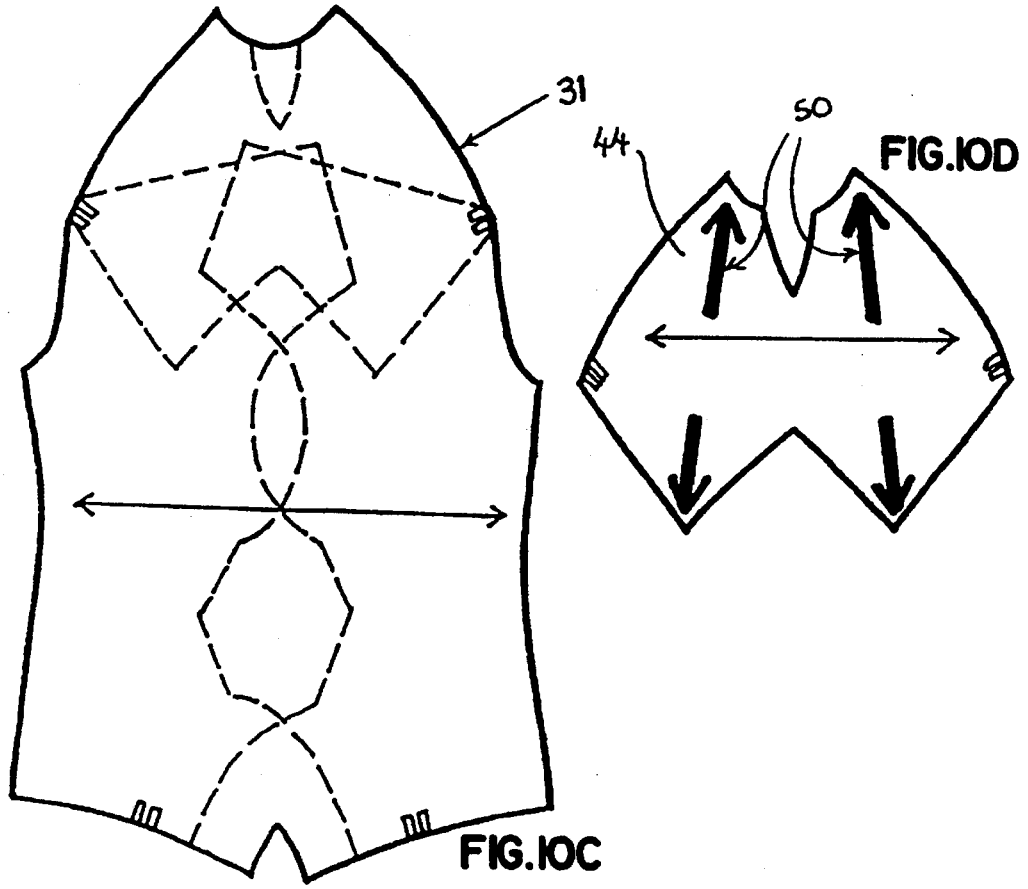
FIG.10C
FIG.10D

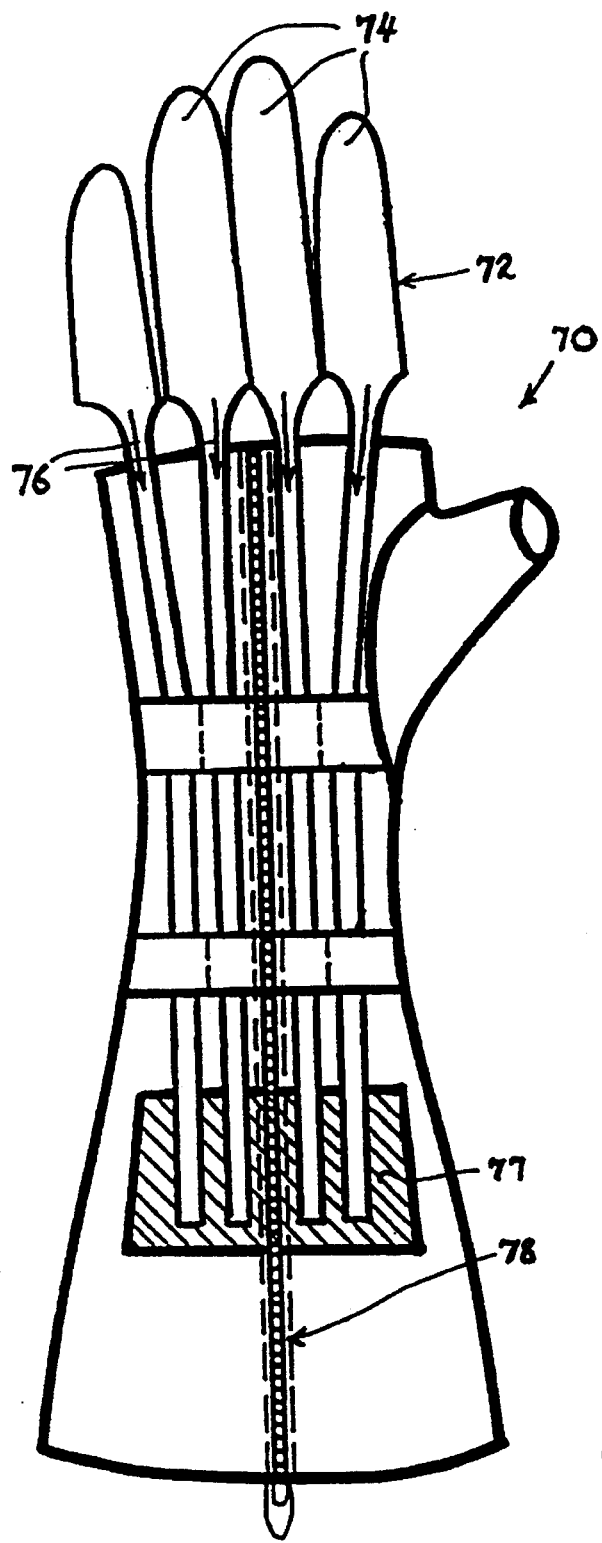
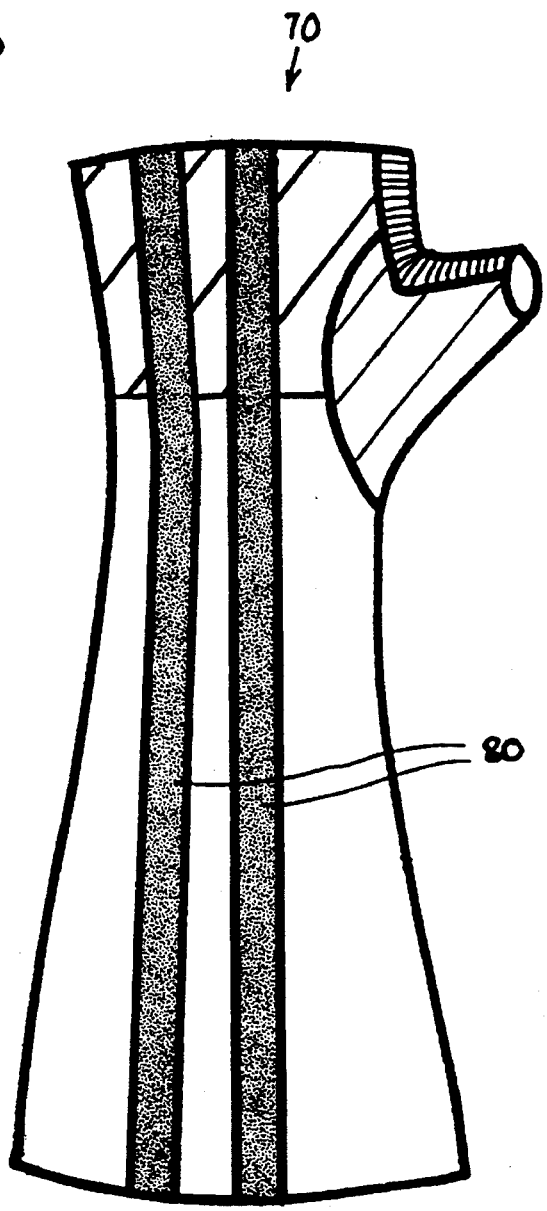
FIG.14A
FIG.14B

DYNAMIC POSTURAL STABILITY SPLINT

FIELD OF THE INVENTION

The present invention relates to a dynamic postural stability splint in the form of a garment and a method of manufacturing same, and relates particularly, though not exclusively, to such a garment for assisting in controlling involuntary muscle movement and providing postural stability for a wearer with cerebral palsy or other neurological dysfunction.

Throughout this specification the terms "posture" and "postural" are used in a general sense to refer to the relative position of parts of the body, whether considered in relation to the body as a whole or in relation to isolated anatomical structures.

BACKGROUND TO THE INVENTION

The present invention will be described with particular reference to its application to people with brain damage syndromes referred to as cerebral palsy. However, it is to be understood that the dynamic postural stability splint according to the invention has wider application such as, for example, in assisting persons with temporary or permanent neuromotor disabilities. It is thought the dynamic postural stability splint can help improve muscle tone of the trunk and extremities and also decrease the degree of associated involuntary movement. Throughout this specification the term "tone" refers to the resistance within muscles to both passive and active movement. Hypotonia is a condition of under activity in the muscle and hypertonia is a condition of over activity in the muscle. Because cerebral palsy is non-reversible, therapy must focus on means of circumventing the effects of the cerebral lesion by surgical, medical or physical interventions. Various types of orthotic devices have been used with a view to preventing orthopaedic complications and functional enhancement, for example, braces and splints which provide support and/or immobilise parts of the wearer's body.

A typical prior art thermoplastic splint is moulded to suit the shape of the wearer's body and provides static support and effectively immobilizes part of the body. There are a number of disadvantages of the conventional static splint. Firstly, the splint does not allow dynamic movement of the part of the body supported by the splint and hence the problem of muscle tone is not adequately addressed. Secondly, the splint is uncomfortable and hot to wear and doesn't allow the skin to breath freely, hence there is a tendency to sweat leading to discomfort, unpleasant body odors and skin maceration and damage. Furthermore, the thermoplastic material tends to soften in hot weather and thus loses its shape.

SUMMARY OF THE INVENTION

The present invention was developed with a view to providing a dynamic postural stability splint capable of effecting both a bio-mechanical change similar to a conventional static splint while simultaneously allowing a degree of dynamic movement of the wearer.

According to one aspect of the present invention there is provided a dynamic postural stability splint in the form of a garment for a wearer with anatomical anomalies, the garment comprising:

a plurality of pieces of flexible elastic material connected together to form the garment and wherein selected pieces of said flexible elastic material are configured and positioned in the garment so as to provide lines of pull applied through circumferential skin contact on the wearer's body in predetermined directions whereby, in use, said garment can provide a bio-mechanical correction of the anatomical anomalies and thereby help to improve postural stability of the wearer.

In one embodiment said garment is in the form of a body suit covering substantially the whole of the trunk of the wearer. The body suit may also cover one or more of the limbs of the body.

In another embodiment said garment is in the form of a glove or gauntlet covering the wrist of a wearer and/or parts of the hand, including the fingers.

In a preferred form of the invention the garment comprises a body suit made from a base material having said selected pieces fastened to the base material, the material of the selected pieces having a higher modulus or coefficient of elasticity than the base material.

According to another aspect of the present invention there is provided a method of manufacturing a dynamic postural stability splint in the form of a garment for a particular wearer with anatomical anomalies, the method comprising the steps of:

obtaining the appropriate body measurements of the wearer including selected detailed circumferential measurements;

assessing the anatomical anomalies of the wearer and prescribing correctional intervention required;

selecting an appropriate flexible elastic material for the garment;

designing a pattern for the garment based on the body measurements obtained including configuring and positioning selected pieces of the pattern so as to provide, in the finished garment, lines of pull through circumferential skin contact on the wearer's body in predetermined directions so as to mimic as closely as possible normal anatomical functions; and, constructing the garment from said flexible elastic material using the pattern thus obtained whereby, in use, the finished garment can help to improve postural stability of the wearer.

Typically the method further comprises the step of reducing the circumferential measurements to obtain the desired firmness of the finished garment on the wearer depending upon age, vascularity, medical condition, degree of involuntary movement and lifestyle considerations.

Preferably said step of designing the pattern for the garment comprises designing a base pattern for the garment and designing separate pattern pieces for the shape and configuration of the selected pieces overlaying the base pattern as reinforcement panels.

Advantageously the selected pieces are cut from a first flexible elastic material and the remainder of the garment is cut from a second flexible elastic material wherein the first material has a higher coefficient or modulus of elasticity than the second material.

According to a still further aspect of the present invention there is provided a method of treating postural instability of a person with anatomical anomalies, the method comprising:

identifying the anatomical anomalies producing the postural instability; and, providing a dynamic postural stability splint in the form of a garment designed to provide lines of pull through circumferential skin contact on the person's body in predetermined directions whereby, in use, the lines of pull can provide a bio-mechanical correction of the physical anomalies to improve postural stability of the person's body.

Preferably said step of identifying the physical anomalies involves identifying distortion and/or dysfunction of a particular anatomical structure, and said step of providing a garment involves ensuring the garment is designed to provide lines of pull which provide correctional intervention to mimic a normal function of the anatomical structure.

Advantageously said method further comprises prescribing a program of wearing said garment whereby, over time, the wearer may relearn normal body functions and patterns of movement under the conditions of improved postural stability that the dynamic splint provides.

Normal body posture is dependent on fixation of anatomical structures (e.g. bone, ligament, tendon, muscle etc.) in a state of balance with themselves and outside forces (e.g. gravity) in static and dynamic posture. Where that balance is not maintained, distortion and dysfunction exist. The dynamic postural stability splint according to the invention attempts to mimic body anatomy in an endeavor to change body dynamics, by re-establishing normal function where such does not exist with the use of elasticised and non-elasticised materials. This occurs as where, for example, a weakened muscle exists on one side of the body and a force will be introduced along that muscle line of action by the splint so as to assist that muscle establish balance with its like muscle group on the opposite body side with an aim of establishing body symmetry.

BRIEF DESCRIPTION OF THE DRAWINGS

In order to facilitate a better understanding of the nature of the invention preferred forms of the dynamic postural stability splint and method of manufacturing same will now be described in detail, by way of example only, with reference to the accompanying drawings in which:

FIGS. 1(a) and (b) illustrate a front and back view respectively of one embodiment of a dynamic postural stability splint according to the present invention in the form of a body suit;

FIGS. 8(a), (b), (c) and (d) illustrate the design lines for selected pieces marked onto the base pattern;

FIGS. 9(a) and (b) illustrate the design lines for selected pieces marked onto the base pattern for the arms;

FIGS. 10(a), (b), (c) and (d) illustrate pattern pieces for the selected pieces and their position on the back body section of the base pattern;

DETAILED DESCRIPTION OF PREFERRED EMBODIMENTS

Figure 2A:
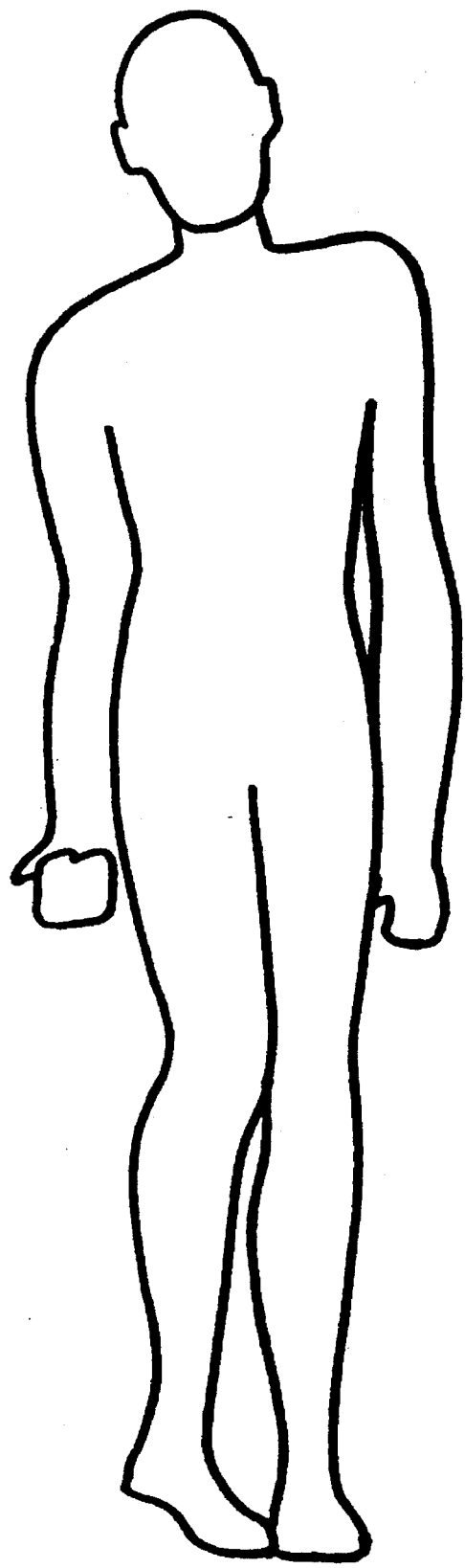
FIGS. 2(a) and (b) illustrate the weight-bearing posture of a child with cerebral palsy for prescription and design of a dynamic postural stability splint.

FIG. 1 illustrates a preferred form of dynamic postural stability splint 10 in the form of a garment having short legs and full length arms. The garment 10 comprises a plurality of panels of flexible elastic material connected together to form a body suit, with selected pieces 12 of the elastic material configured and positioned in the body suit 10 so as to provide lines of pull 14 in predetermined directions on the wearer's body. In use, the garment 10 can help to improve postural stability and to reduce involuntary muscle movement of the wearer since the lines of pull provide a bio-mechanical correction of the relative position and/or orientation of the body parts. Typically the entire garment is made from a suitable stretch fabric and thus the wearer retains a degree of freedom of movement to perform normal body functions.

The dynamic postural stability splint of the present invention is particularly advantageous in its application to children and adolescents with cerebral palsy, since children and adolescents readily adapt to wearing the garments and to relearn normal body functions under the conditions of improved postural stability that the dynamic splint provides.

Figure 2B:
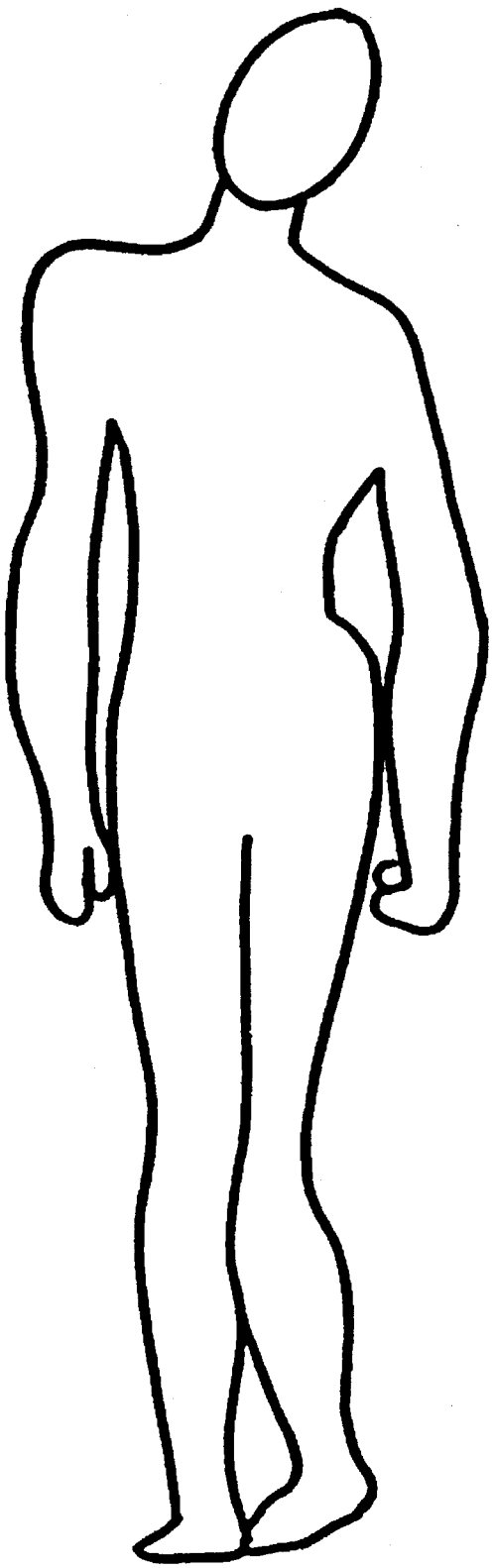

FIG. 2 illustrates a typical weight-bearing posture of a child with cerebral palsy. The first step in providing improved postural stability for this child requires a therapist to identify the physical anomalies and occupational disabilities, and to prescribe appropriate correctional intervention. The child is a 4 year old female with the following physical anomalies:

Head position—anterior dropped to right

Shoulder—internally rotated, scapula winged, dropped and adducted

Elbow—supinated and adducted

Wrist—flexed

Thumb—mid palm

Fingers—flexed

Right Trunk—short, unstable

Right Pelvis—dropped, unstable

Right Femur Head—dropped, internally rotated and adducted

Knee—internally rotated

Ankle—unstable

Toe—walking on toes

The child's cerebral palsy produces the above physical anomalies and has the following detrimental effect on her occupational skills. The child is unable to sit independently on the floor in a normal "W" position. She is unable to move her arm actively and purposely away from the body and engage in activity, which impacts on her ability to play independently and all activities that have an element of fine motor control. Gross right arm movement is possible when well supported and stabilised, however the child has an inability to bring her arm to midline and engage in bilateral hand activities. She is unable to half kneel as her pelvis is unstable which causes her body to collapse and walking is only possible if stabilised in a K-walker with assistance. There is no heel strike on the right side. Her right hand has to be placed and then secured on the walking frame.

Having assessed the posture of the child the therapist then prescribes the following correctional intervention. Shoulder stability can be corrected by a directional and correctional line of pull to approximate gleno humeral junction. The directional line commences one third to two thirds down the arm, both on the anterior and posterior aspects. This directional and correctional line of pull is anchored to the sleeve base. Elbow postural correction is achieved by placing a flexion gusset into the elbow crease to which is attached the forearm component of the sleeve. To override the physical anomaly previously described, this forearm sleeve is also turned between one third to two thirds so that the arm sits at all times in a flexion posture to maximize functional ability.

Trunkal stability is provided by a postural correctional line which extends from the anterior trunk surface up and over the shoulder and continues down the back to L3–4, and also addresses the position of the scapula. Lengthening of the right side of the trunk is achieved by reducing the muscle spasticity of quadratus lumborum, psoas and paravertebral muscles on the left and encouraged by placing the trapezius, rhomboids and levator scapula on the right at anatomical advantage. This is achieved using a directional and correctional line of pull over the scapula to reposition it in a position that will allow optimum function. The stretch fabric material does not limit movement of the scapula within the suit, however it holds it at rest in a more anatomically aligned position. Additional stability may be achieved by placing plastic boning circumferentially around the body. The boning lengths are longer on the right side and shorter on the left side. They are also shorter on the anterior surface and longer on the posterior surface so that medial, lateral and forward flexion of the trunk are not impeded. The plastic boning is flexible and resilient in nature.

Pelvic stability is achieved both by the circumferential base of the splint in addition to the directional and correctional line of pull that continues down from L3–4 over gluteus maximum, gluteus minimus and laterally gluteus medius. The directional and correctional line of pull is spiral in nature, changing the alignment of the femur head in the pelvis. The effect of the spiral directional and correctional line of pull is to reduce the increased tone causing the adduction and allowing the positioning of the femur into neutral with a little abduction.

The approximating of the shoulder girdle with the lengthening of the right side of the trunk, together with the increased pelvic stability, has an impact on the leg length on the right side. Reducing the tone of the adductors of the right hip and decreasing the shortening of the right ham string (both achieved by the directional and correctional line of pull inherent in the splint) results in heel strike and more even leg length.

Based on the above prescription a dynamic postural stability splint in the form of a body suit can then be designed and constructed or this child. The body suit illustrated in FIG. 1 is similar to the body suit prescribed for the child described above, providing the required directional and correctional lines of pull to improve her postural stability. A preferred manner of manufacturing the dynamic postural stability splint 10 of FIG. 1 will now be described with reference to FIGS. 3 to 11.

Figure 3:
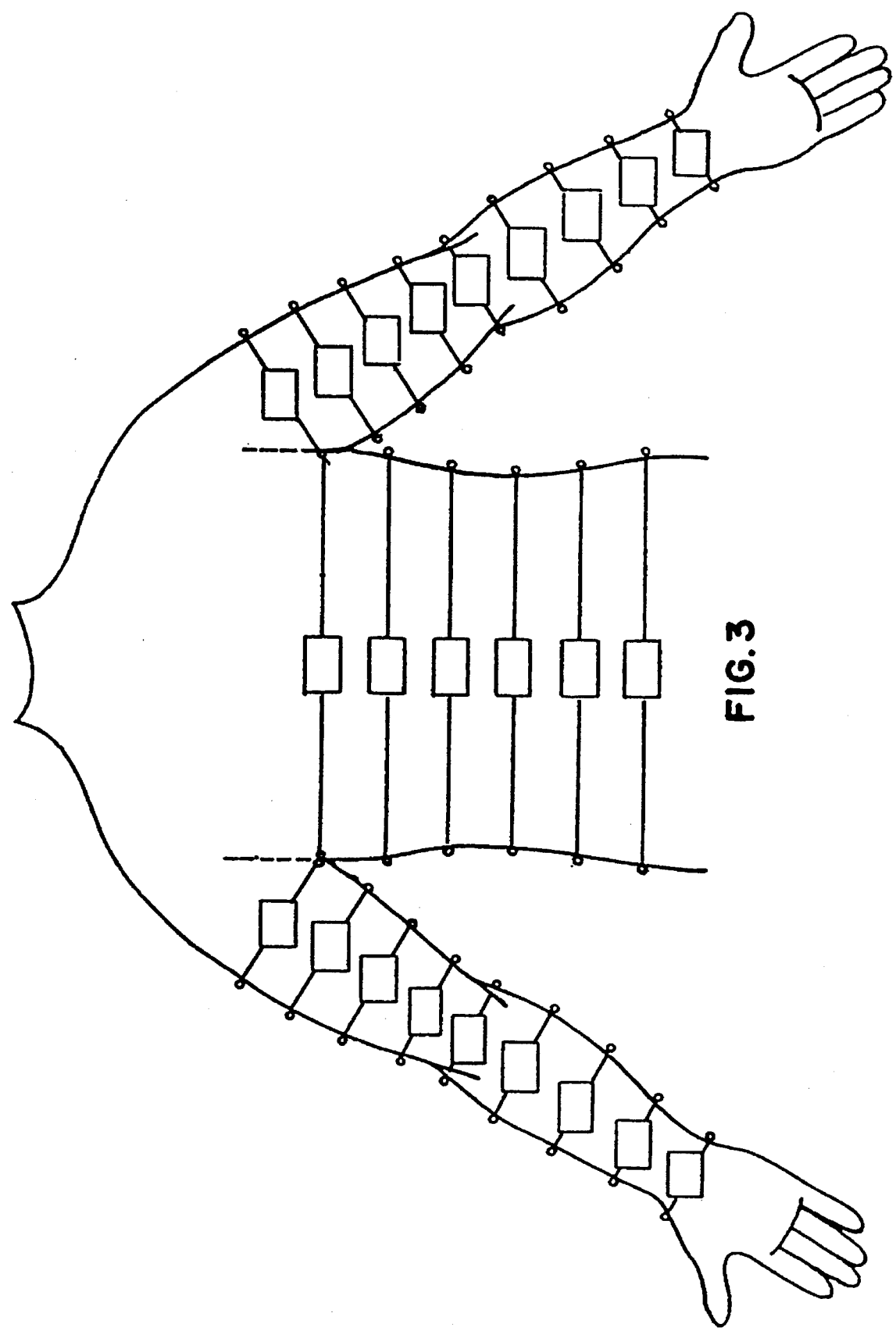
FIG. 3 is an example of a measurement form for recording appropriate measurements, including selected circumferential measurements, of a male upper extremity/torso.

FIG. 3 illustrates a measurement form of the kind used for recording the appropriate body measurements, including selected circumferential measurements, in this case of a male upper extremity/torso for a garment in the form of a vest for a male. Similar body measurements are required for other parts of the body to produce different types of garments. Apart from circumferential measurements about the arms and torso, various length measurements, for example, shoulder to elbow, elbow to wrist, nape to mid chest and underarm to waist, are also required in order to correctly design the garment. It is essential that the measurements are made as accurately as possible in order to ensure that the garment is firmly fitting and comfortable for the wearer. Typically all circumferential measurements are reduced to a predetermined ratio within the range 1:5 to 1:10 dependent upon age, vascularity, medical condition, e.g. Asthma and other respiratory disorders, involuntary muscle movement and lifestyle considerations. A ratio of 1:8 means all circumferential measurements are reduced to 80% of the actual measurement.

A pattern for the garment must then be designed based on the body measurements obtained and the configuration and position of selected panels must be designed, so as to provide, in the finished garment, the prescribed directional and correctional lines of pull. The method of designing the pattern for the garment is based on standard pattern-making techniques modified as follows.

Figure 4:
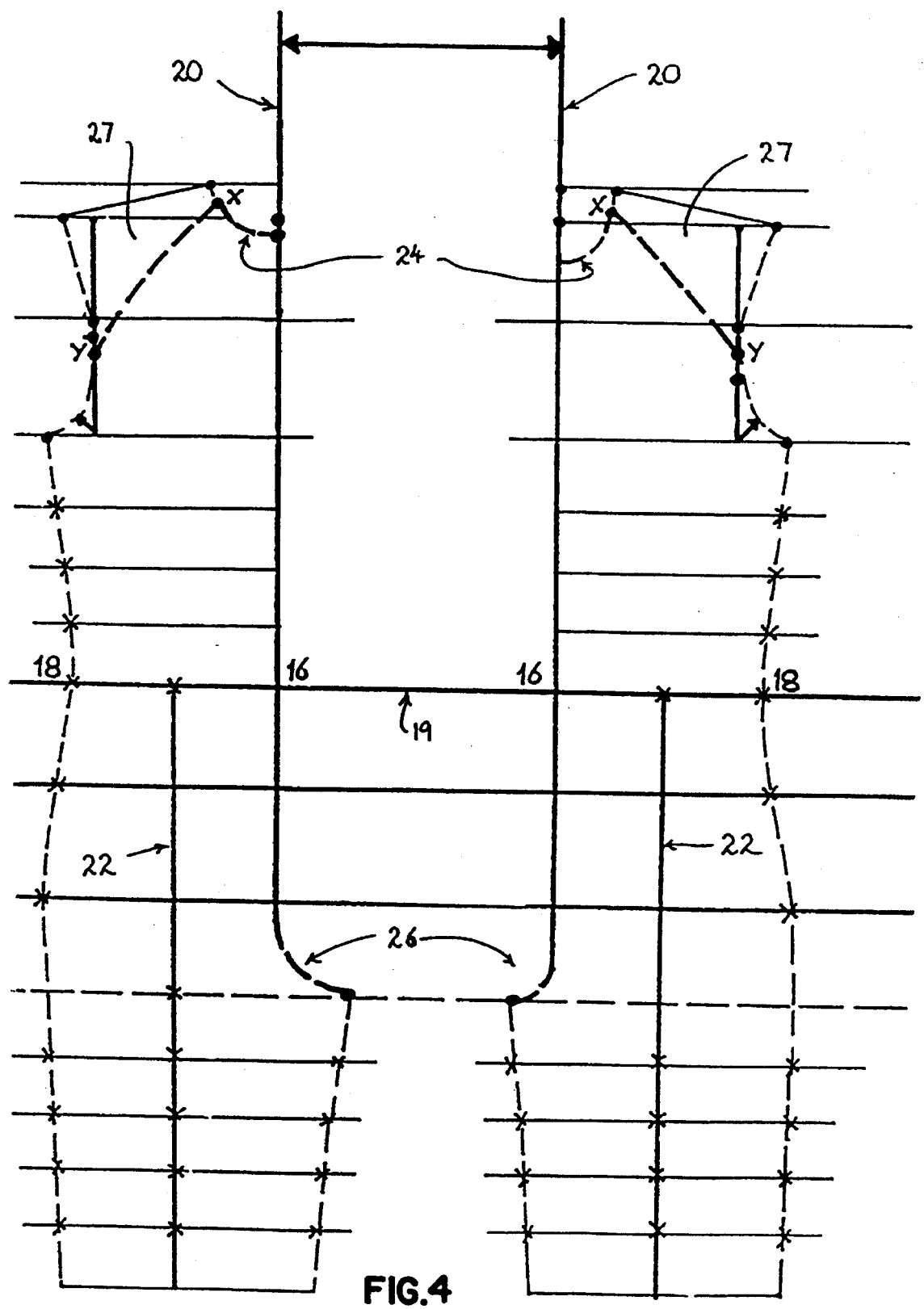
FIG. 4 illustrates a preferred method of designing a base pattern for a dynamic postural stability splint in the form of a body suit.

FIG. 4 illustrates a block construction from which the base pattern for the garment can be derived. The center front block and center back block are constructed as shown in FIG. 4 and the various length and circumferential body measurements are then transferred onto the back and front body blocks in order to arrive at an outline of the base pattern shown in broken lines. Each of the circumferential body measurements is divided by four before being transferred onto the block. Thus, for example, the distance between points 16 and 18 on the front half of the block is equal to one quarter of the actual waist line circumferential measurement. All of the circumferential body measurements are drawn onto the block using the two vertical centre back and centre front lines 20 as reference lines. The circumferential leg measurements are drawn onto the block using two vertical midlines 22, which are drawn substantially parallel to the centre reference lines 20 and commence midway between the points 16 and 18 on the waist line. In the case of the circumferential leg measurements half of the actual leg measurement is transferred onto the two halves of the block.

In order to design the neckline curve 24 and crotch curve 26, appropriately dimensioned curves are drawn on the block, bearing in mind the size of the person's body and other considerations individual to the person. In this instance the neckline curve on the back body block is approximately one fifth of the neck circumference minus 0.25 cm to 0.50 cm, whereas the neckline curve on the front body block is approximately one fifth of the neck circumference minus 0.5 cm to 1.0 cm for this particular person.

Figure 5:
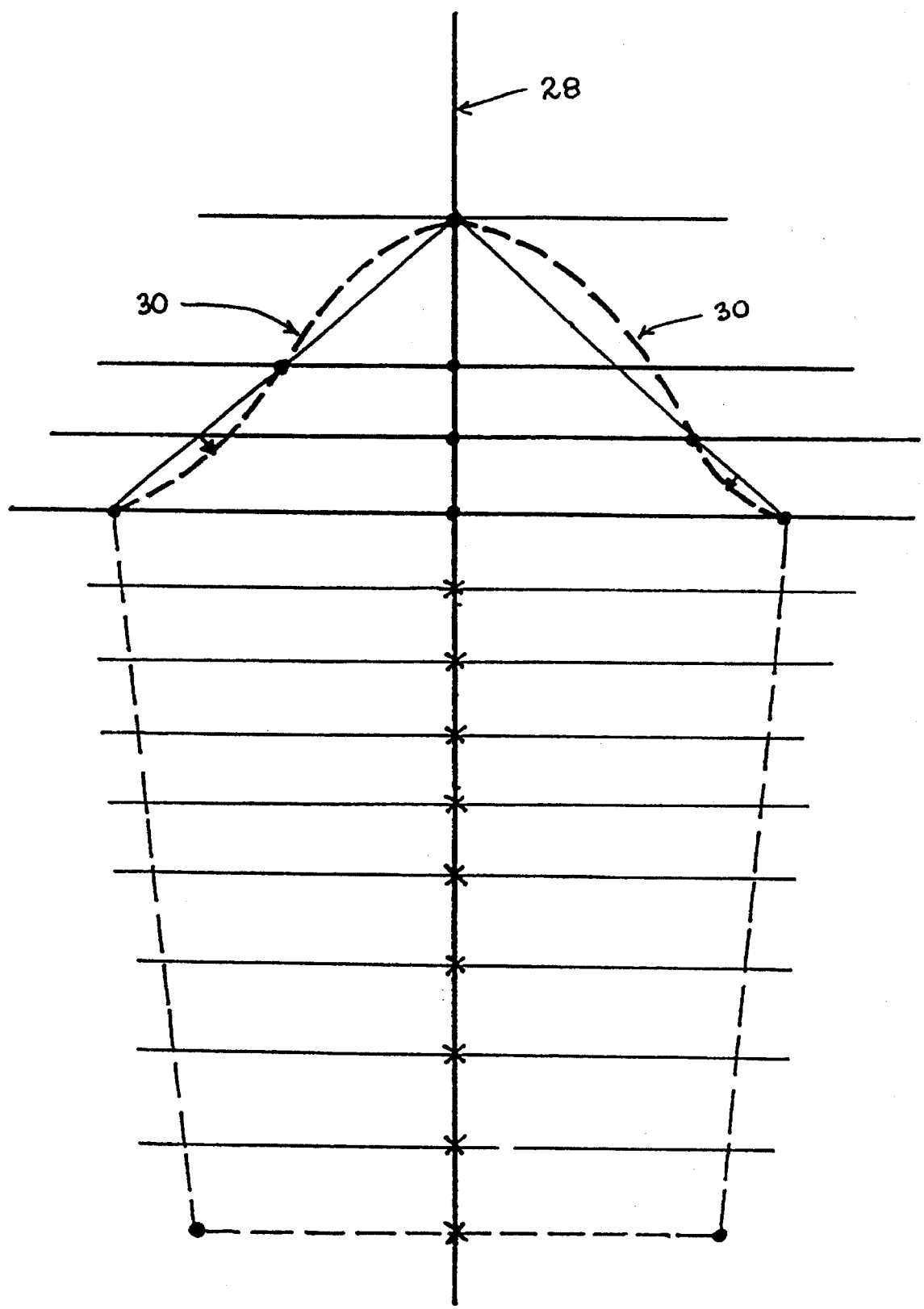
FIGS. 5 and 6 illustrate a preferred method of designing a base pattern for the sleeve of the body suit.
Figure 6:
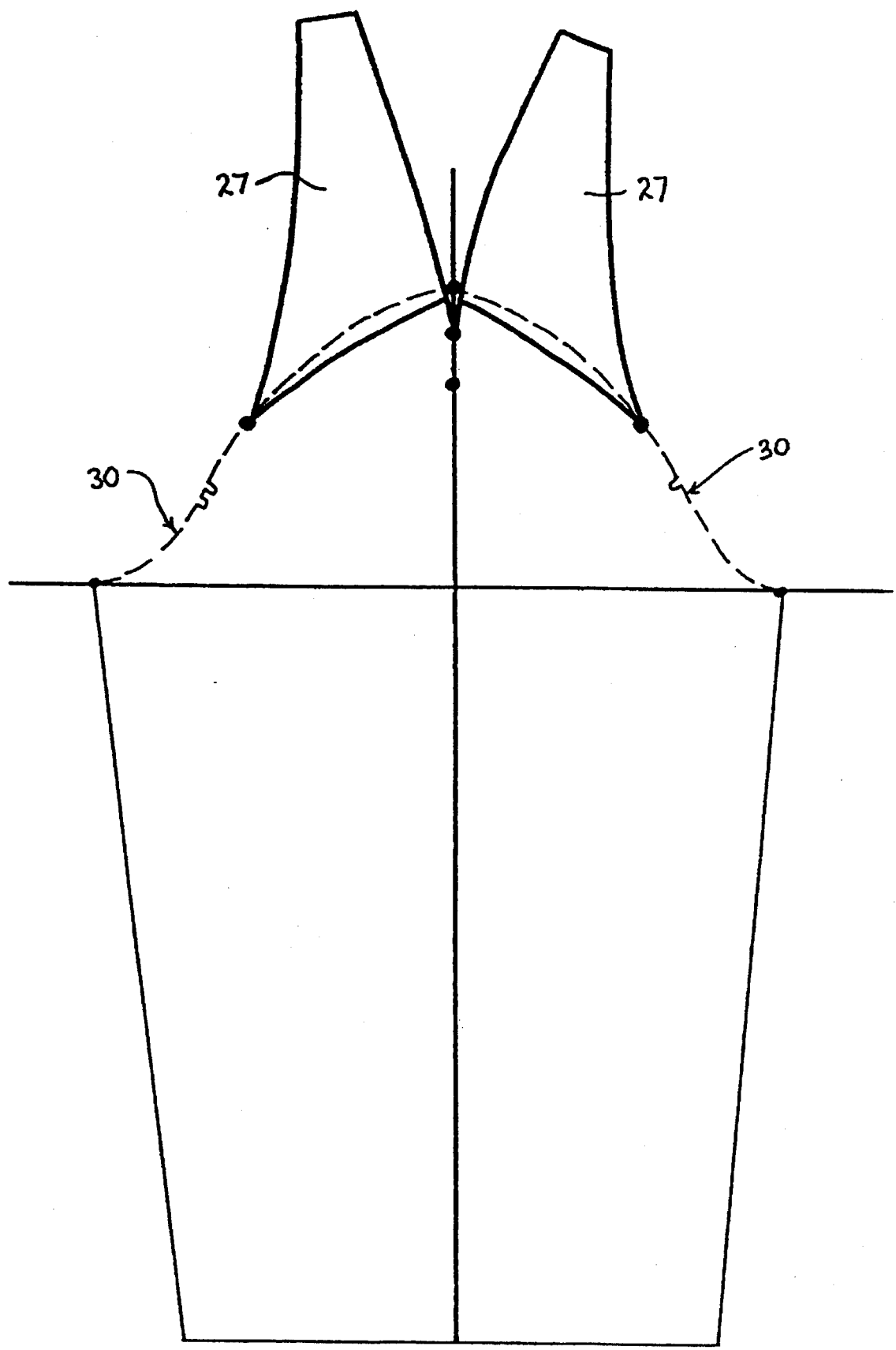

For this particular body suit it was decided to use a raglan sleeve pattern and therefore a section 27 of the front and back shoulder areas of the block must be removed and attached to the head of the sleeves. FIG. 5 illustrates the construction of the sleeve block onto which the appropriate length and circumferential arm measurements are transferred directly using a vertical center line 28 as a reference line. In this case, a full length sleeve is being used. In order to derive the armhole curve 30 of the sleeve the length of the front and back armhole curves on the body block shown in FIG. 4 must be transferred onto the sleeve block. The two sections 27 removed from the front and back shoulder areas of the front and back body blocks are then connected to matching balance points on the sleeve, and the shoulder line is shaped slightly to a point Z as shown in FIG. 6. The sleeve is then divided into two separate pieces by cutting through the center line down to the wrist for a two piece raglan sleeve pattern.

The two piece sleeve block and the front and back body blocks are then traced onto new sheets of paper to obtain the base patterns for the body and sleeves as illustrated in FIGS. 7 and 9 respectively.

The center reference lines 20 on the front and back body base patterns illustrated in FIG. 7 correspond to the center line of the front and back of the garment so that what is illustrated in FIG. 7 is only one half of the front and back sections respectively of the garment. When transferring the pattern onto the material from which the garment is to be made the center reference lines 20 is aligned with a fold line in the fabric material from which the garment is to be made, so that when the fabric is cut in the shape of the front and back body pattern pieces the fabric can then be unfolded to produce the full front and back body sections 29 and 31 respectively of the garment, illustrated in FIGS. 8(b) and (a) respectively.

Typically the garment is provided with an open pubis for ease of independent toileting by the wearer. Accordingly, two crescent-shaped pattern pieces are removed from the back and front body blocks above the crotch point 34. Similarly, in order to ensure comfort in the axillas regions a less aggressive stretch fabric is used, for example, absorbent cotton lycra. Hence, it is also necessary to remove pattern pieces 36 from the front and back body base patterns and the sleeve base pattern to provide room for underarm gussets. The underarm gussets are formed by taking all four of the gusset pattern pieces removed from the body and sleeve base patterns and transferring the measurements of these pattern pieces onto a separate gusset block, (not shown) from which two all-in-one underarm gusset pattern pieces are constructed.

Figures 7A, 7B:
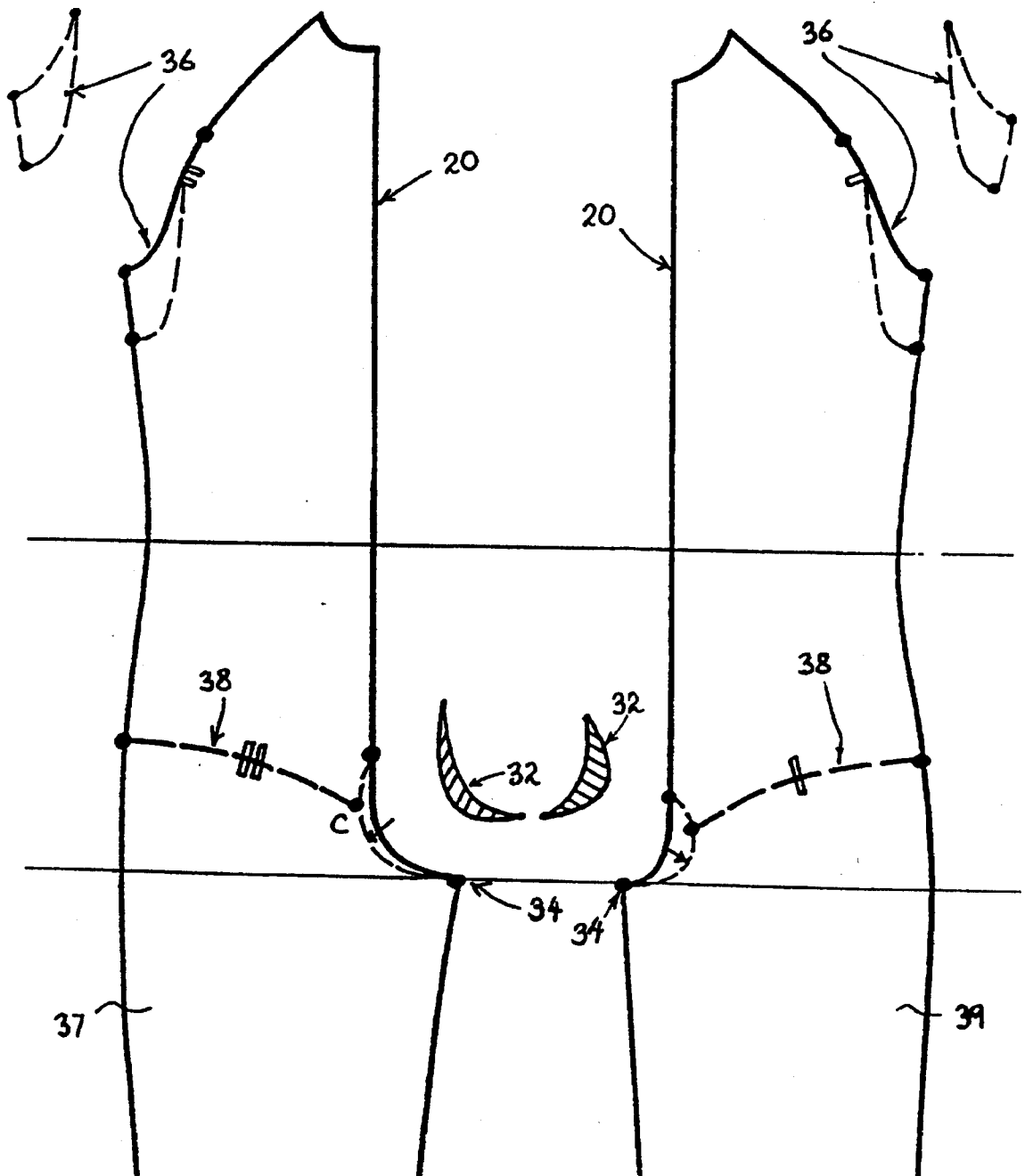
FIGS. 7(a) and (b) illustrate the base pattern for the body and legs of the garment.

The front and back leg sections 39, 37 are separated from the main body pattern pieces by cutting along the brief line 38 on both the front and back body base patterns illustrated in FIGS. 7(a) and (b) respectively. The brief line 38 is a gently curved line drawn in from A to C on the back body base pattern, and from B to D on the front body base pattern, and corresponds to the natural crease line of the body suit when the upper leg is bent upwards at the hip.

The base pattern for the body suit is now completed and the next step is designing the configuration and position of selected panels or pieces. In this embodiment the selected pieces overlay the base pattern and act as reinforcement panels and provide the prescribed correctional lines of pull in the predetermined directions. FIGS. 8(a) and (b) illustrate the back and front body sections 31, 29 of the base pattern respectively with the design lines for the reinforcement panels superimposed thereon. Likewise FIGS. 8(c) and (d) illustrate the left back leg and left front leg sections 37, 39 of the base pattern respectively, and FIGS. 9(a) and (b) illustrate the right back and right front sleeve sections 41, 43 of the base pattern respectively, in each case with the design lines for selected reinforcement panels 12 superimposed thereon. The reinforcement panels 12 provided on the back body section 31 include a left back side panel 40 and a right back side panel 42 which are substantially symmetrical as illustrated in FIGS. 10(a) and (b) respectively. A third reinforcement panel in the form of a back neck piece 44 illustrated in FIG. 10(d) is also provided on the back body section 31. The shape and position of the reinforcement panels is selected in order to achieve the desired correctional lines of pull in the directions predetermined by the correctional intervention prescribed.

Figure 11A:
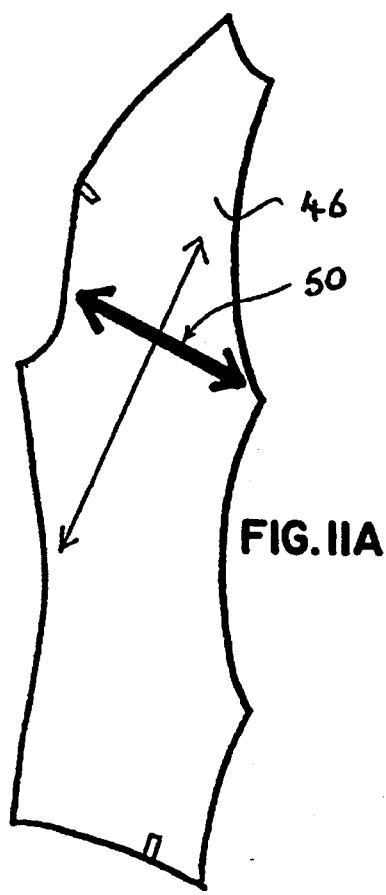
FIGS. 11(a), (b) and (c) illustrate pattern pieces for the selected pieces and their position on the front body section of the base pattern.
Figure 11B:
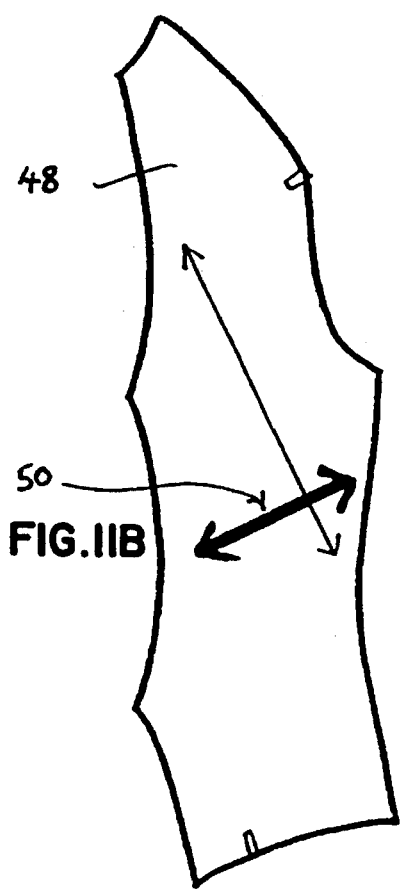
Figure 11C:
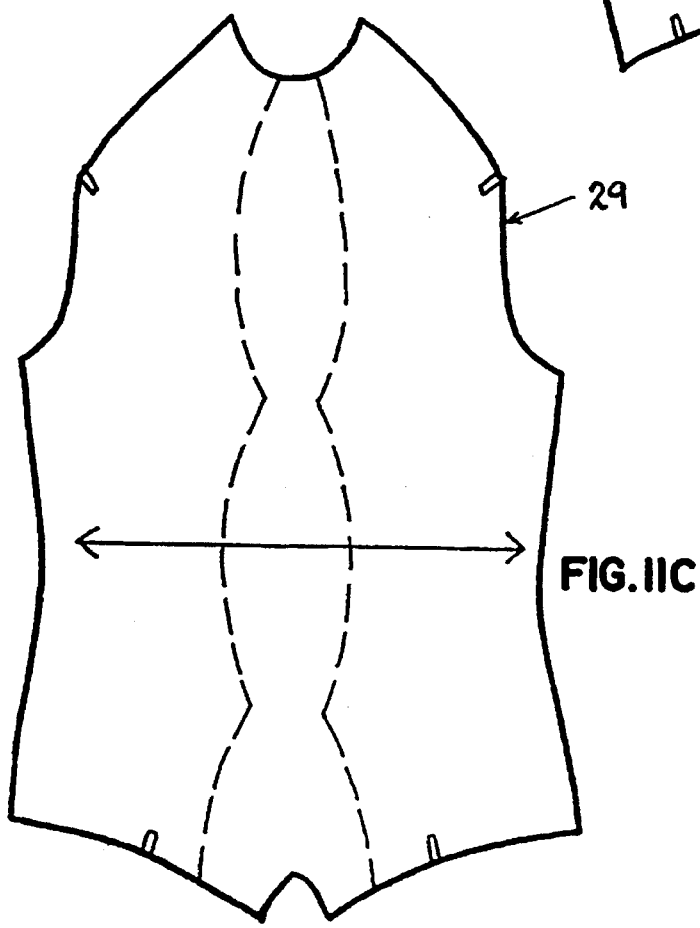

The front body section 29 is provided with two reinforcement panels 12 in the form of a right front side piece 46 and a left front side piece 48 as illustrated in FIGS. 11(a) and (b) respectively, positioned on the front body section 29 as illustrated in FIG. 11(c). In both FIGS. 10 and 11 the lines of pull provided by the reinforcement panels 12 are shown by heavy dark arrows 50. In each case, the reinforcement panels are cut from a suitable flexible elastic material with the grain of the material lying substantially perpendicular to the direction of the lines of pull.

In order to provide the prescribed postural correction for the child illustrated in FIG. 2 the lines of pull need to be directed in a generally upwards direction over the front of the body section, over the shoulders and downwards over the scapula as well as around the waist section over the back of the wearer. Therefore, in this embodiment the reinforcement panels 12 overlap on the back section 31 of the garment in order to anchor the reinforcement panels with respect to each other and to allow the lines of pull to extend from one panel to an adjacent panel, whereas the reinforcement panels 46 and 48 on the front section of the garment do not overlap. It will be appreciated that the left back and left front side panels 40, 48 are joined along one seam and the right back and right front side panels 42, 46 are also joined along one seam so that the lines of pull also extend over the front section and around to the back section in the region of the waist line as can be seen more clearly in FIG. 1. Likewise, the reinforcement panels on the leg sections 37, 39 are joined to the front and back side panels at the brief line so that the lines of pull on the legs are also anchored by the overlapping reinforcement panels on the back body section 31 of the garment. This produces a spiral correctional line of pull as described above, changing the alignment of the femur relative to the pelvis.

Once the design of the reinforcement panels has been drawn onto the base pattern for the front and back body sections, front and back leg sections and front and back sleeve sections, separate pattern pieces can be traced from the base patterns for each of the reinforcement panels.

Typically, the reinforcement panels are cut from a flexible elastic material having a higher coefficient or modulus of elasticity and which is therefore more "aggressive" than the base material of the garment, ie., the reinforcement panels are harder to stretch than the base material. Thus when the garment is worn and the selected reinforcement panels are in a stretched condition they exert definite lines of pull on the wearer's body relative to the base fabric.

Preferably the flexible elastic material employed to manufacture the garment is a stretch fabric of the kind sold under the trademark LYCRA (LYCRA is a registered trademark of Dupont). LYCRA is a fabric with many varying finishes, weights, stretch components and aesthetics. Its primary components are Nylon and Spandex. The higher the percentage of Nylon the more predictable and durable the fabric, whereas a higher percentage of Spandex produces more stretch. POWERNET is a similar stretch fabric having a higher ratio of Nylon to Spandex suitable for the reinforcement panels, whereas SHIMMER is a stretch fabric having a greater Spandex to Nylon ratio than POWERNET and is suitable as a base material. Cotton LYCRA is a soft fabric, non-abrasive combination of cotton and LYCRA and is suitable for axilla gussets and regions of the garment in direct contact with fragile skin.

In the above described embodiment of the dynamic postural stability splint the shape and position of the reinforcement panels 12 is such that they are substantially symmetrical about the center line of the garment. This is because the desired correctional intervention is substantially symmetrical. However, this is by no means essential to the inventive concept and the reinforcement panels can be arranged in non-symmetrical configurations and be of different shapes in order to achieve the required correctional lines of pull in the finished garment. Furthermore, in the above described embodiment the selected pieces 12 are separate from the base material of the garment and overlay the base material as reinforcement panels however, this is by no means essential to the invention as the garment may be constructed in other ways. Although not illustrated in the drawings, the garment is also typically provided with appropriately positioned zip fasteners and/or other fastening devices such as, for example, hook and loop fasteners (VELCRO) to facilitate easy fitting and removal of the garment.

Figures 12A, 12B:
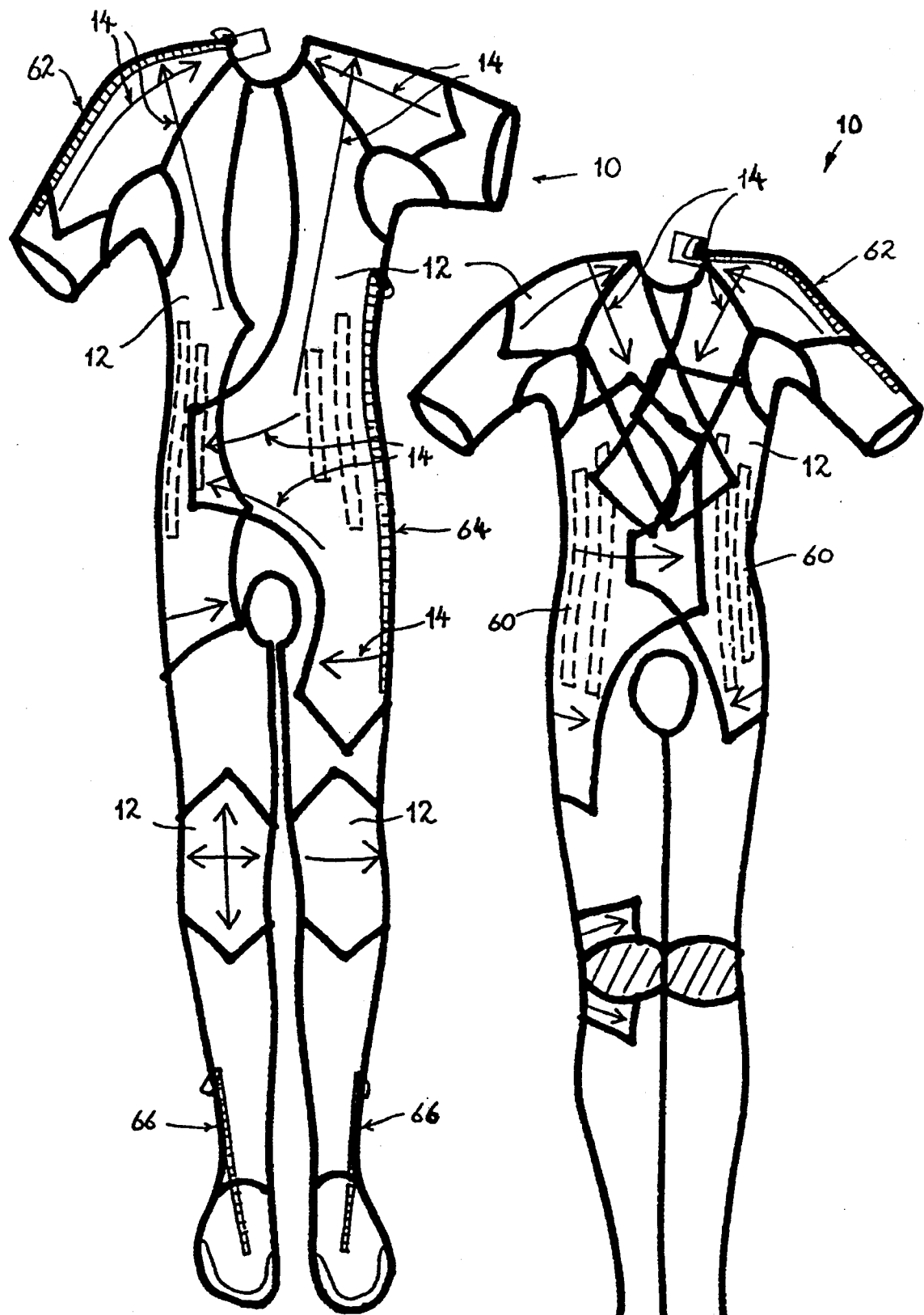
FIGS. 12(a) and (b) illustrate a front and back view respectively of another embodiment of a dynamic postural stability splint.

FIG. 12 illustrates a second embodiment of the dynamic postural stability splint in the form of a garment having full length leg sections and short sleeves, in which the reinforcement panels 12 are of different configuration and non-symmetrical so that the lines of pull in the finished garment are also non-symmetrical. The location of different lengths of plastic boning 60 is also shown in broken outline. The location of several zip fasteners 62, 64 and 66 is also clearly visible in FIGS. 12(a) and (b). Typically, leather is provided on the soles of the feet of a garment of this type in order to increase the longevity of the dynamic splint 10.

Figure 13A:
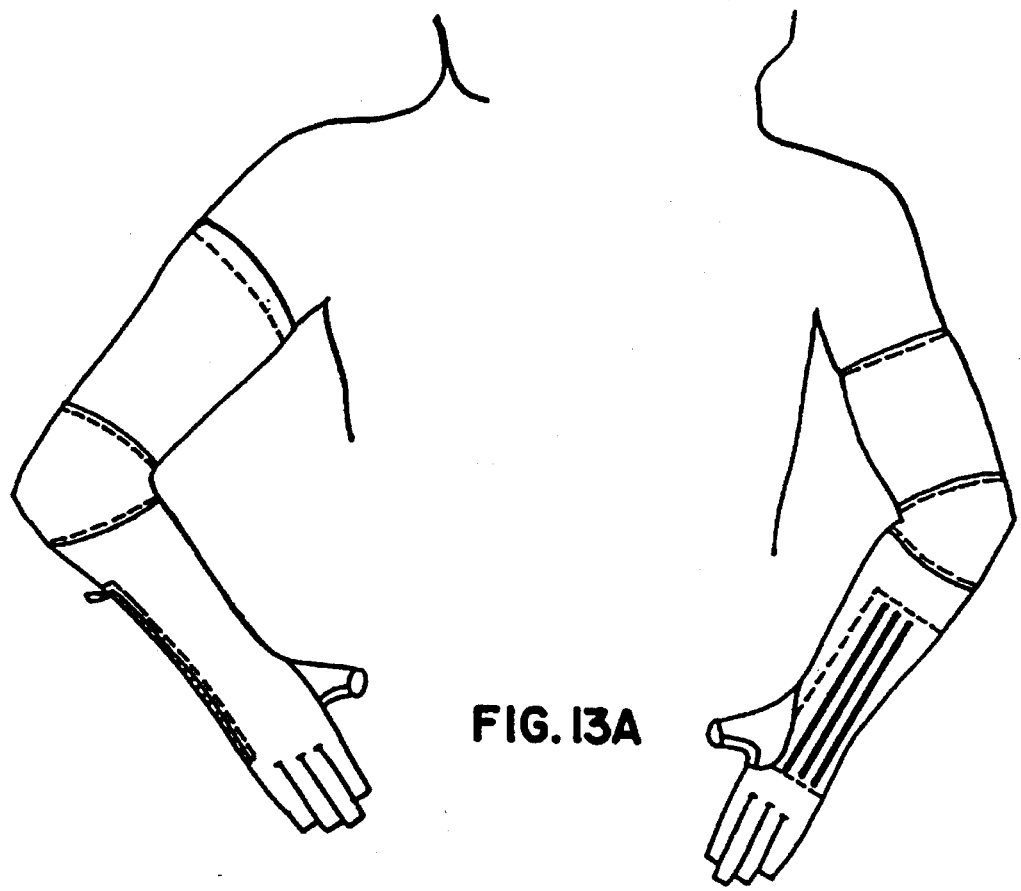
FIGS. 13(a) and (b) illustrate examples of hand and arm dynamic postural stability splints according to the invention; and, FIGS. 14(a) and (b) illustrate the front and reverse side of another embodiment of a hand splint according to the invention.
Figure 13B:
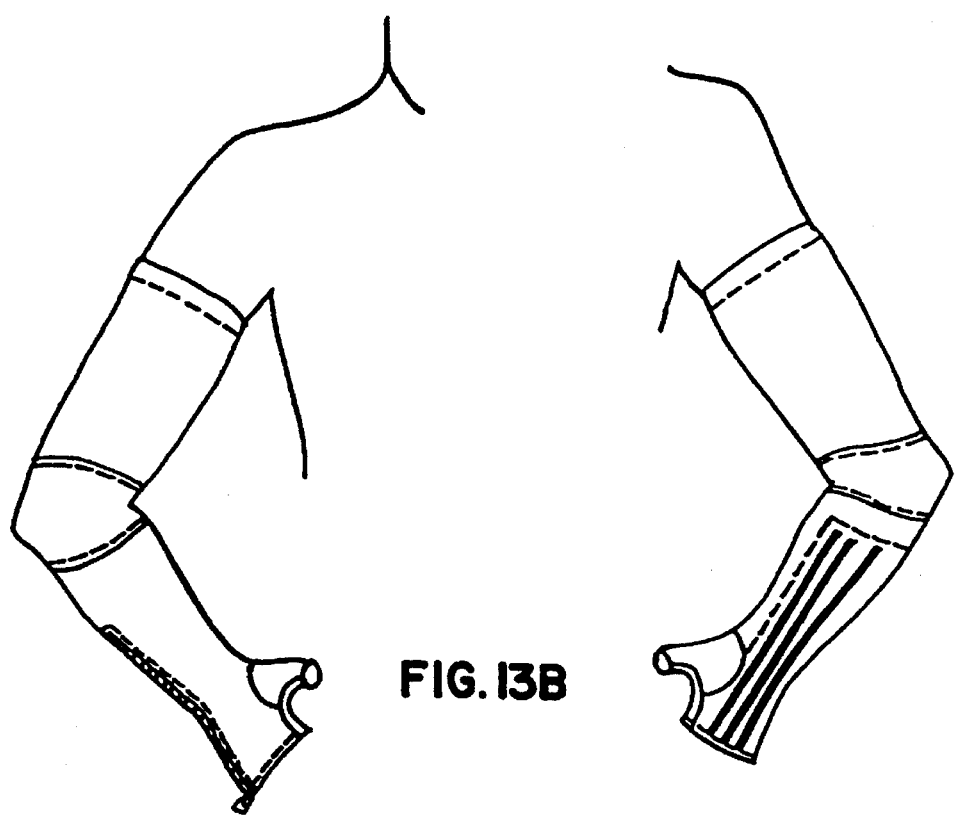

FIGS. 13(a) and (b) illustrate further embodiments of hand and arm splints according to the invention, front and reverse views being shown on the left and right respectively of the sheet. The dynamic postural stability splint of FIG. 13(a) may be distinguished from that of FIG. 13(b) in that the former is provided with fingers whereas the latter is not.

FIG. 14 illustrated a still further embodiment of a dynamic postural stability splint in the form of a glove or gauntlet 70. The gauntlet 70 is designed to provide postural stability of the hand and wrist of a wearer. It comprises a plurality of finger pieces 72 having pods 74 received over the ends of the wearer's fingers and designed to apply directional lines of pull 76 on the fingers of the wearer's hand. The finger pieces 72 are made from elasticized material and are attached to the remainder of the gauntlet by means of a hook and loop (VELCRO) fastener 77 to allow adjustment of the tension applied by each finger pod along the lines of pull 76. A mid-dorsal zip fastener 78 is provided for ease of donning the gauntlet. Plastic boning strips 80 are also provided for support and stability on the palmar surface.

A distinguishing feature of the postural stability splint according to the invention, compared to, for example, prior art pressure garments, is that it is designed to mimic or emulate as closely as possible the normal function of anatomical structures. Thus where weakness exists through failure of osseous, ligamentous, tendinous or muscular tissues, (or any combination of these tissues which may include a joint) that prevents function of the tissue within its physiological norm, either as a result of injury or dysfunction to that local part or as a result of neurological dysfunction or congenital abnormality, a garment can be produced which mimics the normal function of the non-functional or aberrant structures. For example, muscle may be assisted by the use of elasticised materials which operate in tandem with the affected muscle along the path between its' origin and insertion. The material being so tensioned as to assist the muscle in its normal function. Materials of a rigid or semirigid nature may be acting in tandem with the anatomical norm to emulate the function of bone. Ligament may be emulated by the use of variable stretch materials fashioned so as to mimic normal ligament and tendon sheaths, with passage provided where necessary for a second material sewn in a manner and positioned so as to mimic the anatomy and physiology of normal tendon. Either singularly or in combination this allows the affected body part to move in a direction predetermined by the designer either to assist function and/or produce a therapeutic response.

Now that preferred embodiments of the dynamic postural stability splint and method of manufacturing same have been described in detail, it will be apparent that the dynamic splint according to the invention represents a significant improvement over prior art static splints. The dynamic postural stability splint according to the invention has the following advantages:

(1) It provides an immediate improvement in postural stability of the wearer (2) It may improve muscle tone of the trunk and extremities (3) It helps to decrease the degree of involuntary muscle movement (4) It may improve respiratory function (5) It can help to improve gross motor patterns of movement (6) An appropriately designed garment can improve hand function (7) It facilitates functional independence in the performance of daily occupational tasks (8) It can enhance the wearer's self esteem.

Numerous variations and modifications will suggest themselves to persons skilled in the pattern making or dress making arts as well as persons in the helping professions such as occupational therapists and physiotherapists, other than those already described, without departing from the basic inventive concepts. For example, in the illustrated embodiments the dynamic postural body splint is in the form of a body suit, however the principles of the invention can be applied to produce any appropriate garment that will provide the desired correctional intervention. For example, the dynamic postural stability splint may be in the form of a glove, sleeve, vest, tight or any other suitable garment. Furthermore, although the garment according to the preferred embodiment is manufactured from suitable stretch fabrics, the dynamic postural stability splint according to the invention can be made from any suitable flexible elastic material. All such variations and modifications are to be considered within the scope of the present invention, the nature of which is to be determined from the foregoing description and the appended claims.

I claim:

1. A method of manufacturing a dynamic postural stability splint in the form of a garment for a particular wearer with anatomical anomalies caused by neurological dysfunction, the method comprising the steps of:

obtaining the appropriate body measurements of the wearer including selected circumferential measurements;

assessing the anatomical anomalies of the wearer and prescribing correctional intervention required;

selecting an appropriate flexible elastic material for the garment;

designing a pattern for the garment based on the body measurements obtained including configuring and positioning selected pieces of the flexible elastic material so as to provide, in the finished garment, lines of pull applied to an affected anatomial structure through circumferential skin contact on the wearer's body in predetermined directions so as to provide a biomechanical correction of the anatomical anomalies, wherein said configuring and positioning step includes the step of configuring and positioning said selected pieces on the wearer's body so as to provide lines of pull from a point of origin to a point of insertion of an affected muscle or muscle group so as to increase range of motion and thereby assist the affected muscle group in its normal function; and, constructing the garment from said flexible elastic material using the pattern thus obtained such that, in use, the finished garment can help to improve postural stability of the person's body.

2. A method of manufacturing a dynamic postural stability splint as claimed in claim 1, the method further comprising the step of reducing the circumferential measurements to obtain the desired firmness of the finished garment on the wearer depending upon age, vascularity, medical condition, degree of involuntary movement and lifestyle considerations.

3. A method of manufacturing a dynamic postural stability splint as claimed in claim 1, wherein said step of designing the pattern for the garment comprises designing a base pattern for the garment and designing separate pattern pieces for the shape and configuration of the selected pieces overlaying the base pattern as reinforcement panels.

4. A method of manufacturing a dynamic postural stability splint as claimed in claim 3, wherein the selected pieces are cut from the flexible elastic material with the grain of the material lying substantially perpendicular to the desired direction of the lines of pull in the finished garment.

5. A method of manufacturing a dynamic postural stability splint as claimed in claim 4, wherein the selected pieces are cut from a first flexible elastic material and the remainder of the garment is cut from a second flexible elastic material wherein the first material has a higher coefficient or modulus of elasticity than the second material.

6. A method treating postural instability of a person with anatomical anomalies, the method comprising:

identifying the anatomical anomalies producing the postural instability; and, providing a dynamic postural stability splint in the form of a garment, the garment including a plurality of pieces of flexible elastic material connected together, with selected pieces of said flexible elastic material configured and positioned to provide lines of pull applied through circumferential skin contact on the person's body in predetermined directions such that, in use, the lines of pull can provide a bio-mechanical correction of the physical anomalies to improve postural stability of the person's body, wherein said selected pieces of flexible elastic material are configured and positioned to provide lines of pull from a point or origin to a point of insertion of an affected muscle or muscle group so as to increase range of motion and thereby assist the affected muscle group in its normal function.

7. A method of treating postural instability as claimed in claim 6, wherein said step of identifying the physical anomalies involves identifying distortion and/or dysfunction of a particular anatomical structure, and said step of providing a garment involves ensuring the garment is designed to provide lines of pull which provide correctional intervention to mimic as closely as possible a normal function of the anatomical structure.

8. A method of treating postural instability as claimed in claim 6, wherein said method further comprises prescribing a program of wearing said garment whereby, over time, the wearer may relearn normal body functions and patterns of movement under the conditions of improved postural stability that the dynamic splint provides.

* * * * *